United States Patent [19]

Beresnev et al.

[11] Patent Number: 4,855,563
[45] Date of Patent: Aug. 8, 1989

[54] DEVICE FOR PLASMA-ARC CUTTING OF BIOLOGICAL TISSUES

[76] Inventors: Alexei S. Beresnev, ulitsa Ostrovskogo, 6, kv. 59; Leonid A. Serykh, ulitsa Oktyabrskoi Revoljutsii, 7, kv. I06, both of Smolensk; Viktor S. Saveliev, ulitsa Donskaya, 27, kv. 29, Moscow; Valery S. Volkoedov, ulitsa Marshala Ustinova, I6, korpus 2, kv. 908, Moscow; Igor V. Stupin, ulitsa Akademika Bakuleva, 4, kv. I22, Moscow, all of U.S.S.R.

[21] Appl. No.: 228,699

[22] PCT Filed: Aug. 11, 1986

[86] PCT No.: PCT/SU86/00077

§ 371 Date: Apr. 8, 1988

§ 102(e) Date: Apr. 8, 1988

[87] PCT Pub. No.: WO88/01218

PCT Pub. Date: Feb. 25, 1988

[51] Int. Cl.$^4$ .............................................. B23K 15/00
[52] U.S. Cl. ........................ 219/121.39; 219/121.48; 219/121.5; 219/121.52; 219/75; 313/231.31
[58] Field of Search ............... 219/121.39, 121.48, 219/121.5, 121.51, 121.52, 74, 75, 76.16; 239/79; 313/231.31, 231.41, 231.51

[56] References Cited

U.S. PATENT DOCUMENTS 2,862,099 11/1958 Gage ................................ 219/121.5
3,914,573 10/1975 Muehlberger ................... 219/121.5
4,118,618 10/1978 Gauthier et al. ................ 219/121.5
4,250,373 2/1981 Tanidai ............................ 219/121.5
4,369,919 1/1983 Beloev et al. ......................... 239/79
4,620,080 10/1986 Arata et al. .................... 219/121.52
4,748,312 5/1985 Hatch et al. ..................... 219/121.5

FOREIGN PATENT DOCUMENTS 2450659 3/1980 France .
275261 10/1970 U.S.S.R. .

OTHER PUBLICATIONS

Elektrodugovve Plazmotrony, Novosibirsk, 1980, pp. 34–35.

Primary Examiner—M. H. Paschall
Attorney, Agent, or Firm—Lilling & Greenspan

[57] ABSTRACT

The device includes a cathode assembly (1) having a housing (3) and an electrode (6) with a tapering portion (19), and an anode assembly (2) having a housing (20) and a nozzle (12) receiving the tapering portion (19) of the electrode (6), the nozzle (12) successively defining a cylindrical chamber (11), a tapering chamber (21), an arcing chamber (7) and a plasma jet forming chamber (23). The smaller end of the frustoconical tapering portion (19) of the electrode (6) is the end face of the electrode (6) received in the cylindrical and tapering chambers (11 and 21) so that the distance from the end face of the electrode (6) to the arcing chamber (7) equals 0.1 to 0.5 of the length of the tapering chamber (21), and the length of the tapering portion (19) of the electrode (6) is 3.5 to 4.5 times the diameter of the electrode (6).

1 Claim, 1 Drawing Sheet

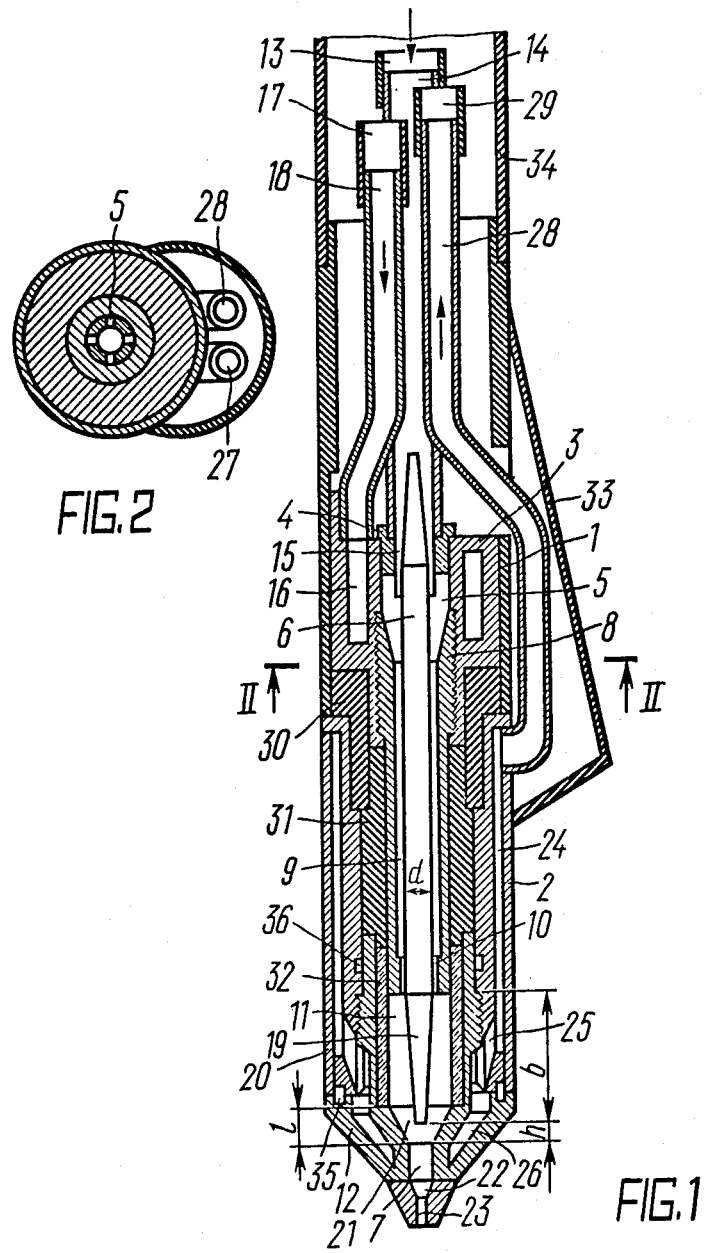

DEVICE FOR PLASMA-ARC CUTTING OF BIOLOGICAL TISSUES

BACKGROUND OF THE INVENTION

1. Field of the Invention

The invention relates to medical instrumentation, and more particularly it relates to devices for plasma-arc cutting of biological tissues.

2. Description of the Prior Art

It is possible to use for cutting biological tissues various devices wherein either an indirect arc or a microplasma arc is formed.

There is known a plasma-arc cutting device including a housing accommodating therein a cathode assembly and an anode assembly. The anode assembly includes a nozzle of a complicated shape, receiving an electrode having its pointed end facing the direction of forming an electric arc. The cathode assembly has channels for feeding a plasma-forming gas (Advertising Manual "Elektrodugovyie plazmotrony", Novosibirsk, 1980, pp. 34–35).

Devices of this kind are unsuitable for cutting biological tissues, as their microplasma jet is of a power inadequate for maintaining a required speed of cutting biological tissues; furthermore, they are rated for operation with a relatively high working pressure of the plasma-forming gas, which results in excessive saturation of biological tissues with the gas. The temperature of the plasma jet produced by this known device is within 5000° C., which is insufficient for cutting biological tissues and causes heat lesions of the biological tissues at the side of the cut to a considerable depth.

There is further known a device for plasma-arc cutting of biological tissues, likewise comprising a cathode assembly and an anode assembly. The electrode of the cathode assembly has a tapering portion having its pointed end facing the area of generation of the electric arc. The cathode assembly has passages formed therein for supplying the plasma-forming gas. The anode assembly has a nozzle receiving the tapering portion of the electrode, the nozzle successively defining a cylindrical chamber, a tapering chamber, an arcing chamber and a plasma arc forming chamber, in the quoted order (SU, A No. 275261, Beresnev A. S. et al., 1970, Bulletin No. 22).

In this device, however, the arcing process in the arcing chamber is insufficiently stable at low flow rates and pressure of the plasma-forming gas, which shortcoming should be eliminated to make the device suitable for applications in medicine. Moreover, under these conditions the anode spot eventually moves from the arcing chamber into the tapering chamber of the nozzle, which results in the dropping voltage at the arc and its diminishing power, impairing the cutting and coagulating properties of the plasma jet. To restore the anode spot into the arcing chamber, it is necessary to step up the working pressure of the plasma-forming gas, e.g. to $2 \times 10^5$ Pa, and then to reduce it once again to the working feed pressure of $1 \times 10^5$ Pa. However, this periodic increasing of the working pressure of the gas results in an increasing velocity of the issuing plasma jet, complicating the surgeon's task and threatening injuries to organs not being operated upon.

SUMMARY OF THE INVENTION

The invention has for its aim the creation of a device for plasma-arc cutting of biological tissues, wherein an improved structure of the anode assembly should provide for stable arcing at relatively small feed rates and pressure of the plasma-forming gas.

This object is attained in a device for plasma-arc cutting of biological tissues, wherein the cathode assembly includes a housing with passages for supplying the plasma-forming gas and an electrode accommodated in the housing and having a tapering portion, and the anode assembly includes a housing and a nozzle receiving the tapering portion of the electrode, facing the area of generation of the plasma jet, the nozzle successively defining a cylindrical chamber, a tapering chamber, an arcing chamber and a plasma jet forming chamber. In accordance with the invention, the tapering portion of the electrode is of a frustoconical shape, its smaller end which is the end face of the electrode facing the area of generation of the plasma jet, the electrode being received in the cylindrical and tapering chambers so that the distance from the arcing chamber to the end face of the electrode equals 0.1 to 0.5 of the length of the tapering chamber, and the length of the tapering portion of the electrode is 3.5 to 4.5 times the diameter of the electrode.

It is expedient that the passages for supplying the plasma-forming gas should have a length substantially equal to the length of the plasma jet forming chamber of the nozzle, and should be spaced from the end face of the electrode substantially by the length of its tapering portion.

BRIEF DESCRIPTION OF THE DRAWINGS

The invention will be further described in connection with an embodiment thereof, with reference being made to the accompanying drawings, wherein:

FIG. 1 is a longitudinal sectional view of a device for plasma-arc acutting of biological tissues, embodying the invention; and FIG. 2 is a sectional view of the same device, taken along line II—II of FIG. 1.

DESCRIPTION OF THE PREFERRED EMBODIMENT

The device for plasma-arc cutting of biological tissues includes a cathode assembly 1 (FIG. 1) and an anode assembly 2. The cathode assembly 1 includes a housing 3 having press-fitted therein a collet 4 with slits 5 acting as gas supply passages. The collet 4 holds inside it an electrode 6 fixed in a required position with respect to the top margin of the arcing chamber 7 by an unsplit bushing 8.

The bushing 8 likewise has gas supply passages 9 and 10 formed therein for supplying the plasma-forming gas into the cylindrical chamber 11 of a nozzle 12.

The cathode assembly 1 is provided with a gas connection 13 communicating via a tube 14 with passages 15 for supplying the plasma-forming gas in the collet 4.

Furthermore, the cathode assembly 1 has a passage 16 for supplying a coolant coming via a connection 17 and a tube 18. The electrode 6 has a tapering portion 19 of a frustoconical shape, the smaller end of this frustoconical portion being the end face of the electrode 6.

The anode assembly 2 includes a housing and the abovementioned nozzle 12 defining thereinside a cylindrical gas chamber 11, a tapering chamber 21 and a plasma-forming channel 22 made up by the arcing chamber 7 and a plasma jet forming chamber 23.

The anode assembly is cooled by a coolant fed through its passages 24 and 25, and also through a passage 26 encompassing the nozzle 12. The coolant is fed via a connection 27 (FIG. 2) and returned via a tube 28 and connection 29 (FIG. 1).

The cathode and anode assemblies 1 and 2 are electrically insulated from each other by insulating members 30, 31, 32, 33 and 34.

The nozzle 12 has a threaded portion for connection with the anode assembly 2. The end portion of the anode assembly and its internal part have grooves cut therein for sealing gaskets 35 and 36, the sections of these gaskets being selected so as to provide for easy screwing in of the nozzle 12 to the required position, while sealing away the device from ingress of the coolant into its working spaces, with the coolant feed pressure being 2.5 atm. or higher (in a tightness test).

The bottom end part of the bushing 8 is so shaped as to retain the electrode 6 in the tapering chamber 21 of the nozzle 12 with respect to the top end of the arcing chamber 7 by screwing the bushing 8 into the housing 3 of the cathode assembly 1. In this required position the electrode 6 has its tapering portion 19 received in the chambers 11 and 21, its end face facing the plasma jet forming area. The distance "h" from the arcing chamber 7 to the end face of the electrode 6 is selected to equal 0.1 to 0.5 of the length "l" of the tapering chamber 21. The distance should not be short of 0.11, as this has found to affect stable arcing and impair thermal stability of the electrode; neither should it be in excess of 0.51 (h>0.51), as in this case the arc would be ignited only at exceedingly high feed rates of the plasma-forming gas.

The length "b" of the tapering portion 19 of the electrode 6 is selected to be 3.5 to 4.5 times its diameter "d", and it should not be smaller than 3.5d, as this has been found to effect stable arcing; on the other hand, with the length being in excess of 4.5d (b>4.5d), stable arcing requires exceedingly high feed rates of the plasma-forming gas.

In the embodiment being described, the coolant is tap water fed at a pressure not short of 0.6 atm. and not higher than 1.5 atm. The use of coolant feed pressures beyond the stated range is ill-advised, as with the pressure being short of 0.6 atm. the degree of cooling of the nozzle 12 is inadequate and the arcing is unstable, and with the pressure higher than 1.5 atm. the load of the sealing gaskets 35, 36 is stepped up, leading to their eventual failure. Should the sealing properties of the gasket 36 be impaired, water would enter the gas chamber 11, breaking electric insulation of the electrode 6 with respect to the anode assembly 2. This threatens an electric breakdown, with an electric arc being ignited between the side surface of the electrode 6 and the housing 20 of the anode assembly 2.

The device for plasma-arc cutting of biological tissues is operated, as follows.

First, the device is adjusted by checking the operating order of the nozzle 12 and setting the electrode 6 in the bushing 8 in the chamber 21 at the required distance of about 0.4–0.5 mm from the entrance to the arcing chamber 7.

A required supply rate of the plasma-forming gas is set, the coolant feed is turned on, and the arcing voltage is switched on.

The coolant flowing via the connection 29 and tube 28 enters the passages 24, 25 and 26, cooling the anode assembly 2 and its nozzle 12, also flowing from the channel 24 via the connection 27 into the channel 9, to cool the electrode 6 and the cathode assembly 1, and to leave the device via the connection 17. However, the circulation of the cooling water can be reversed, as shown in the appended drawing, FIG. 1, and mentioned hereinabove.

The plasma-forming gas is supplied to the connection 13 of the tube 14, to flow via the slits 5 and passage 9 into the cylindrical gas chamber 11 of the nozzle 12. Stable arcing in the chamber 7 at its entire surface at low supply pressures of the gas (below 0.1 atm.) and its low supply rates is maintained owing to the optimized ratio of the length of the tapering portion 19 of the electrode 6 to its diameter and optimized positioning of the electrode 6 in the tapering chamber 21 of the nozzle 12 relative to the arcing chamber 7, as well as by the taper of the tapering chamber 21, the remoteness of the passages 10 from the arcing chamber 7 and the length of these passages 10 being matched to the length of the plasma jet forming chamber 23.

With the coolant and plasma-forming gas being supplied to the device, the gas gap between the end face of the electrode 6 and the cylindrical surface of the arcing chamber 7 of the nozzle 12 is broken down and ionized, with voltage being supplied across the electrode 6 and nozzle 12 from a constricted-arc power supply source. The arc is initially ignited with a low supply current and a low gas supply rate, to avoid flashes at the arc ignition moment and to afford time for warming up the anode assembly 2. This accomplished, the arcing current is raised to the working value, and the supply rate of the plasma-forming gas is adjusted to obtain a plasma jet of the required parameters.

The disclosed design of a torch, i.e. of a device for plasma-cutting of biological tissues, provides for cutting biological tissues efficiently and reliably with very low pressures and low supply rates of the plasma-forming gas, allowing for low velocities of the issuing plasma jet variable within a broad range.

The invention can be employed in surgery, e.g. in operations of dissecting tumors and coagulating blood vessels at the sides of incisions.

We claim:

1. A device for plasma-arc cutting of biological tissues, comprising a cathode assembly having passages for supplying a plasma-forming gas and a conical electrode; an anode assembly the nozzle of which comprises an arcing chamber arranged successively with a plasma jet-forming chamber, wherein the electrode has the shape of a truncated cone which has a tapering portion the length of which is equal to between 3.5 and 4.5 its diameter and the end of said electrode is arranged in a tapering chamber of the nozzle at a distance from said arcing chamber of 0.1 to 0.5 times the length of said tapering chamber, and the passages supplying the plasma-forming gas of the cathode assembly having a length equal to the length of the plasma jet-forming chamber and are spaced from the end of the electrode by the length of the tapering portion of the electrode.

* * * * *